US 11,440,057 B2

United States Patent
Greeley

(10) Patent No.: US 11,440,057 B2
(45) Date of Patent: Sep. 13, 2022

(54) PUPAE SINGULATOR AND SEX SORTER

(71) Applicant: Verily Life Sciences LLC, South San Francisco, CA (US)

(72) Inventor: Daniel Greeley, San Francisco, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 72 days.

(21) Appl. No.: 16/924,885

(22) Filed: Jul. 9, 2020

(65) Prior Publication Data

US 2021/0008600 A1 Jan. 14, 2021

Related U.S. Application Data

(60) Provisional application No. 62/872,844, filed on Jul. 11, 2019.

(51) Int. Cl.
*B07C 5/36* (2006.01)
*A01K 29/00* (2006.01)
(Continued)

(52) U.S. Cl.
CPC .............. *B07C 5/36* (2013.01); *A01K 29/00* (2013.01); *A01K 67/033* (2013.01); *B07C 1/04* (2013.01); *B07C 5/342* (2013.01)

(58) Field of Classification Search
CPC .. A01K 29/00; A01K 67/033; A01K 67/0332; A01K 67/0335; A01K 67/0339;
(Continued)

(56) References Cited

U.S. PATENT DOCUMENTS 3,223,237 A * 12/1965 Harrod, Jr. ........... A01K 67/033
209/675
6,143,496 A * 11/2000 Brown ................. C12Q 1/6806
436/805

(Continued)

FOREIGN PATENT DOCUMENTS

CN 105123623 12/2015
CN 107838054 3/2018
(Continued)

OTHER PUBLICATIONS

Hock, "Improved Separator for the Developmental Stages, Sexes, and Species of Mosquitoes", Available online at: http://johnwhock.com/products/laboratoryequipment/larvalpupal-separator/, Model 5412 Instructions, vol. 17, No. 6, Dec. 30, 1980, 1 page.
(Continued)

*Primary Examiner* — Gene O Crawford
*Assistant Examiner* — Muhammad Awais
(74) *Attorney, Agent, or Firm* — Kilpatrick Townsend & Stockton LLP

(57) ABSTRACT

Devices, systems, and methods for isolating an insect pupa from an aqueous solution including a plurality of insect pupae. An isolation device may include a primary channel through which the aqueous solution and insect pupae travel, an outlet, and a secondary channel that intersects the primary channel. The secondary channel may transport a fluid to add it to the primary channel between an inlet and the outlet. When the sealable outlet is closed, an insect pupa located downstream of the intersection of the primary and secondary channels remains stationary while any insect pupae upstream of the intersection are pushed towards the inlet. The systems and methods described herein may also provide for identifying and sorting insect pupae.

35 Claims, 8 Drawing Sheets

(51) Int. Cl.
*A01K 67/033* (2006.01)
*B07C 1/04* (2006.01)
*B07C 5/342* (2006.01)

(58) Field of Classification Search
CPC .. A01K 67/04; B07C 1/04; B07C 1/10; B07C 1/14; B07C 5/36; B07C 5/342
USPC .......................................................... 209/577
See application file for complete search history.

(56) References Cited

U.S. PATENT DOCUMENTS

| | | | |
|---|---|---|---|
| 7,452,725 B2 * | 11/2008 | Leary ..................... | G01N 15/14 436/63 |
| 8,025,027 B1 | 9/2011 | Morales-Ramos et al. | |
| 9,242,219 B2 * | 1/2016 | Bull ......................... | C10J 3/466 |
| 10,342,222 B2 | 7/2019 | Sobecki et al. | |
| 2015/0008163 A1 | 1/2015 | Nimmo et al. | |
| 2018/0049418 A1 * | 2/2018 | Leo ...................... | A01K 67/033 |
| 2018/0206473 A1 | 7/2018 | Massaro et al. | |

FOREIGN PATENT DOCUMENTS

| | | | | |
|---|---|---|---|---|
| CN | 108526042 | | 9/2018 | |
| CN | 108620306 | | 10/2018 | |
| CN | 209073276 | | 7/2019 | |
| CN | 209073276 U | * | 7/2019 | ........... A01K 67/033 |
| WO | 2019078785 | | 4/2019 | |
| WO | WO-2019078785 A1 | * | 4/2019 | ........... A01K 67/033 |

OTHER PUBLICATIONS

International Application No. PCT/US2020/041657, International Search Report and Written Opinion, dated Oct. 13, 2020, 13 pages.
Application No. CN202010667655.X , Office Action, dated Nov. 1, 2021, 11 pages.
Application No. PCT/US2020/041657 , International Preliminary Report on Patentability, dated Jan. 20, 2022, 12 pages.

* cited by examiner

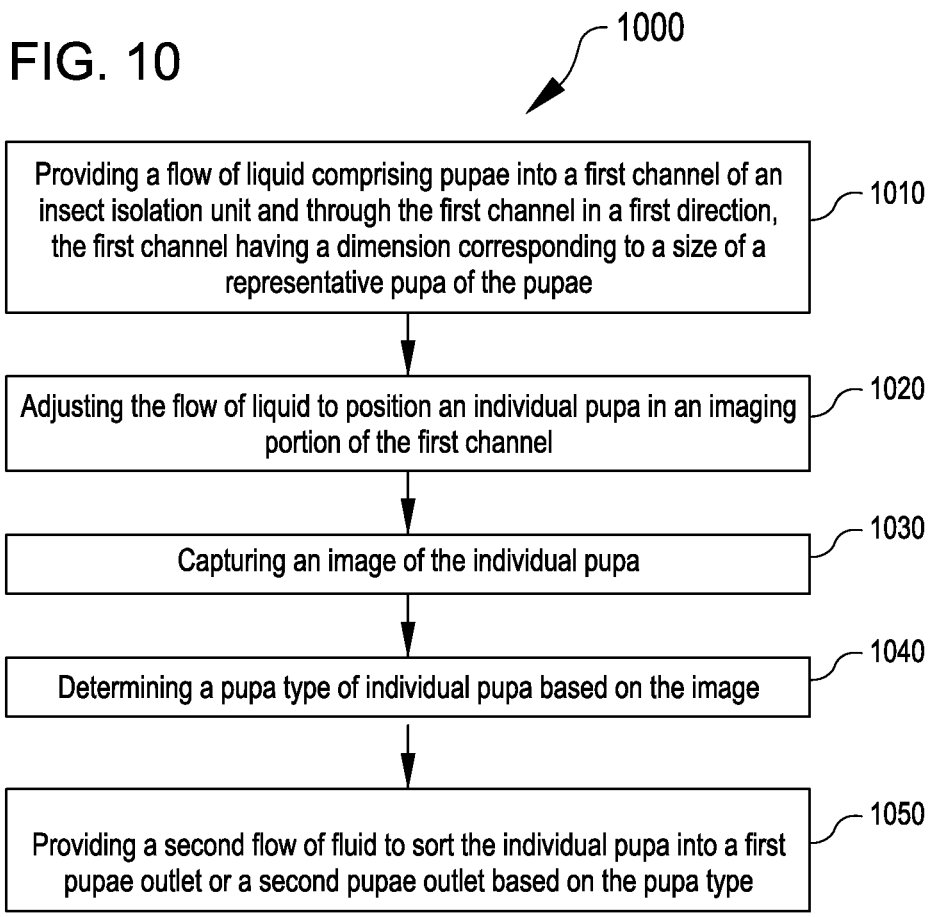

PUPAE SINGULATOR AND SEX SORTER

CROSS-REFERENCE TO RELATED APPLICATIONS

This application claims priority to U.S. Provisional Patent Application No. 62/872,844, filed on Jul. 11, 2019, titled "Pupae Singulator," the contents of which are hereby incorporated by reference in their entirety.

BACKGROUND OF THE INVENTION

Many Sterile Insect Technique (SIT) programs require visually classifying insects to separate male and female insects because male-only releases are more effective at introducing sterility into wild populations. Typically, sex-sorting batches of insects is an involved and human reliant process that involves a human visually inspecting each insect at an adult stage and sorting accordingly or limited purity mechanical sex-sorting methods based on sexually dimorphic traits such as body size in the pupal stage (e.g. sieving). Some other classifications, such as species, insect type, or size are similarly time and resource intensive and require human sorting of individual insects or mechanical separation with limited accuracy.

For some insects, the male and female pupae vary in size, and groups thereof may be sorted based on size or on at least some of the characteristics described above but with limited purity as many of these traits vary widely within sexes. Small females and large males, for example, can be misclassified in mechanical processes without time-consuming human inspection. Isolating and observing the pupae to differentiate males and females that overlap in body size or other sexually dimorphic traits, however, may prove difficult and time-consuming for human selection and sorting.

BRIEF SUMMARY OF THE INVENTION

A system of one or more computers that can be configured to perform particular operations including sorting insect pupae by virtue of having software, firmware, hardware, or a combination of them installed on the system that in operation causes or cause the system to perform the actions. One general aspect of the insect pupae sorting system, includes an isolation device having a first channel with an inlet and an outlet to deliver a first flow of liquid including insect pupae and a second channel that intersects the first channel between the inlet and the outlet to deliver a second flow of liquid into the first channel. The second flow of fluid intersecting the first flow generates a third flow of liquid and separates adjacent insect pupae being transported through the first channel. The insect pupae sorting system also includes an optical sensor positioned proximate to the outlet of the isolation device to capture images of pupae from the third flow of liquid. Downstream of the optical sensor, the system also includes a storage unit system coupled to the outlet that includes a container into which insect pupae of a first type are directed based at least in part on the captured images.

In another general aspect, an insect pupae isolation device is described including: a body; a first channel formed in the body for transporting a first flow of fluid including insect pupae, the first channel having a first dimension corresponding to a size of the insect pupae and having an inlet at a first end of the first channel and an outlet at a second end of the first channel. The insect pupae isolation device also includes a second channel formed in the body, having a second dimension smaller than the first dimension, that meets the first channel at an intersection positioned between the inlet and the outlet to deliver a second flow of fluid into the first channel to generate a third flow of liquid and to separate adjacent insect pupae being transported through the first channel.

In another general aspect a method of sorting insect pupae is described, including providing a flow of fluid with insect pupae into a first channel of an insect isolation device. The isolation device has a first channel along which the insect pupae travel in a first direction, the first channel having a dimension corresponding to a size of a representative pupa of the insect pupae. The method also includes providing a second flow of fluid, through a second channel, into the first channel. The method further includes determining that an individual pupa has passed the second channel and capturing an image of the individual pupa. The method also includes determining a pupa type of the individual pupa based on the image and sorting the individual pupa based on the pupa type.

In at least one example, an insect pupae sorting system is described, having an isolation device with a first channel having an inlet and an outlet and a second channel intersecting the first channel between the inlet and the outlet. The insect pupae sorting system also includes a cover that encloses the first channel and the second channel into fully-enclosed passages. The system includes an optical sensor to capture an image of an insect pupa in the isolation device. The insect pupae sorting system also has a storage system including at least one holding tank in fluid communication with the isolation device and a processor configured to determine the insect pupa has passed the second channel, receive an image of the insect pupa from the optical sensor, determine a pupa characteristic based on the image, and cause the insect pupa to travel into holding tank of the storage system based at least in part on the pupa characteristic.

In another example, a method of imaging an individual insect pupa includes directing a flow of aqueous solution including insect pupae into a first channel having a dimension corresponding to a size of a representative insect pupa. The method includes providing a stream of fluid, through a second channel, into the first channel and closing an outlet of the first channel after an individual insect pupa of the insect pupae has passed the second channel. The method also includes capturing an image of the individual insect pupa.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 10 illustrates an example process for imaging and sorting insect pupae, according to at least one example.

DETAILED DESCRIPTION OF THE INVENTION

Figure 1:
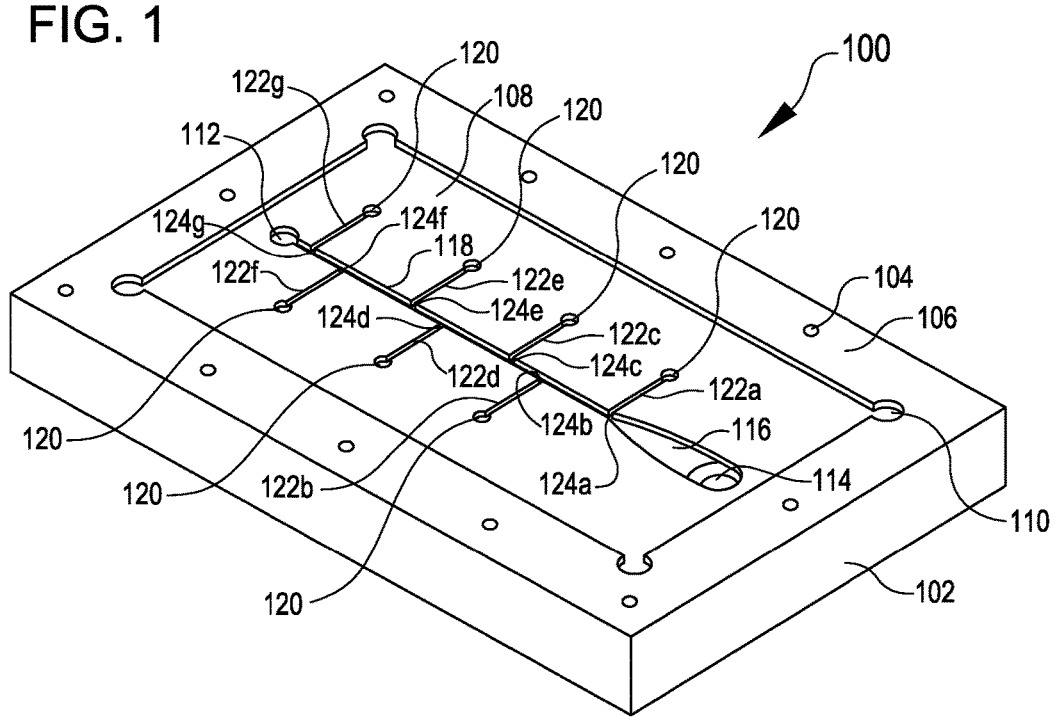
FIG. 1 illustrates an isolation device for isolating individual insect pupae according to at least one example.

Examples are described herein in the context of insect isolation and classification at the pupa stage. Those of ordinary skill in the art will realize that the following description is illustrative only and is not intended to be in any way limiting. For example, isolation systems and techniques described herein can be used with a variety of identification and classification systems and techniques. Examples described herein relate to classifying mosquitoes in the pupa stage, though the techniques described herein can be used to classify other insects or mosquitoes in other stages. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Current methods of sorting mosquitoes typically involve waiting for mosquitoes to mature to the adult stage and visually sex sorting by singulating the adults down a lane. Sorting mosquitoes at the pupal stage has been limited to sorting large groups of pupae using a sieve or using a laboratory tool referred to a Hock's separator (e.g., Larval-Pupal Separator). Use of the sieve may be automated, but is limited to sorting by size. The Hock's separator can sort based on different characteristics, but requires a human to manually operate the tool and is not designed for high throughput. The devices, systems, and methods described herein provide a fast and efficient method for sex sorting insects at a pupal stage based on any suitable characteristic. The insects are sorted while in an aqueous solution. Because the insects are in the pupal stage, they can be carried in the aqueous solution to isolate and sort into separate containers. At the pupal stage, the insects may be manipulated or transported with less effort and potential damage to insects than with adult insects.

It is difficult, using current methods and systems, to isolate individual insects from a large population for classifying and sorting. Current methods typically involve waiting passively for adult insects to travel along a certain path. The methods and systems described herein provide the ability to isolate an individual insect pupa out of a population of pupae and actively transport that individual insect rather than waiting for the insect to move along a desired path on its own. This improves the efficiency and throughput of systems for classifying and sorting insects. The isolation and sorting systems herein may be automated and performed or operated by a computing device to quickly identify and sort insects.

In an illustrative example, an insect sorting system includes an isolation device, an optical sensor, and a storage unit system. The isolation device is used to isolate an individual pupa out of a flow of solution or fluid having many pupae therein. The isolation device relies on the introduction of additional fluid flow into the flow of solution having pupae therein to increase a distance between adjacent pupae within the flow. Once an individual pupa is isolated and singulated in the isolation device, an image may be captured or the pupa may be viewed for certain characteristics to identify and classify the pupa. Once the pupa is identified or classified, it is routed within the storage unit system to a container, an additional processing step is performed (e.g., maturing the pupa into an adult for distribution in SIT programs), or the pupa is disposed of.

In some examples, the isolation device includes a primary channel or passage defined by a groove in a solid material. The primary channel has an inlet and an outlet and transports a flow of fluid including pupae while the outlet is open from the inlet to the outlet. A secondary channel, also defined by a groove in the solid material, intersects the primary channel. The secondary channel has a separate inlet and delivers an additional fluid flow into the primary channel between the inlet and the outlet. As an individual pupa passes the location where the secondary channel intersects the primary channel, the fluid delivered by the secondary channel will cause the individual pupa to accelerate through the primary channel, or increase a gap or distance between the individual pupa and an adjacent pupa traveling down the primary channel. Once the individual pupa has passed the intersection of the primary channel and the secondary channel, as detected by a sensor such as an optical sensor, optical gate, or light curtain, a computer may shut the outlet to cease the flow of liquid comprising pupae out of the outlet. Once the outlet is closed, the fluid introduced by the secondary channel will backflush or push fluid and pupae upstream of the intersection of the primary channel and the secondary channel out of the isolation device, thereby isolating the individual pupa for imaging, classification, or sorting.

Once isolated, the individual pupa are imaged for determining a characteristic such as size or sex by which the pupa are later sorted. Insect pupa sex can be identified by visual inspection of their sex organs. Male pupa have different genitalia at the tail of the pupa. It may also be possible to identify the sex of the pupa by the antennae as male and female adult mosquitoes have different size and shaped antennae. Another important characteristic is size, the male pupae and female pupae are of different sizes so imaging or other determination of the size of the pupae can be used to determine the sex of the pupae. In some cases, multispectral imaging of the individual pupa, once isolated using the systems and method described herein, may assist in determining a sex and thereby sorting insect pupae according to sex or some other characteristic.

The techniques described herein are described with reference to mosquito pupae but are applicable to other insects and other stages, such as larval stages of insects. For example, some larvae exhibit physical sexual differences which may be observed using the methods described herein. For instance, with some insects, at larval stage 3 the males and females begin to develop visually different antennae which may be observed.

This illustrative example is given to introduce the reader to the general subject matter discussed herein and the disclosure is not limited to this example. The following sections describe additional non-limiting examples and techniques relating to using a pupa isolation device for classifying insects.

Turning now to the figures, FIG. 1 illustrates an isolation device 100 for isolating a single pupa from a flow of fluid including many pupae for classification and sorting, according to at least one example. An upper surface 106 of the base 102 includes a recessed portion 108 and recessed corners 110 to receive a plate of clear material (not shown) such as a piece of glass. The clear plate may be secured to the base 102 and sealed such that fluid does not escape from the primary channel 118 or secondary channels 122. Additionally, the clear plate may be sealed in such a manner that it can withstand pressure applied by the fluids. This allows pupae within the isolation device 100 to be viewed through the plate. In this example, the recessed corners 110 help ensure that the plate such as a rectangular piece of glass will fit into the corner without reshaping or requiring additional work to achieve a square corner in the recessed portion; however, while this particular configuration for the base 102 is used in this example, any suitable shape to accept a plate may be employed. Further, the base 102 may not require a recess to secure the plate. Instead, the plate may in affixed to an upper surface of the base 102 and sealed as described above, e.g., using a silicone, rubber (buna rubber), plastic welding, caulking, rubber cement, glazing compounds, epoxy, or other non-toxic material. The upper surface 106 of the base 102 in this example also includes holes 104 which may be threaded for securing the plate to the base 102, though any suitable coupling means may be employed, including screws, rivets, adhesives, clamps, etc.

The base 102 defines a primary channel 118 through which a flow of fluid, such as an aqueous solution, and pupae or other stages of insects (e.g., larvae) may be introduced. The primary channel 118 enters the base 102 at an inlet 114. The inlet 114 may include a threaded or barbed connection to connect to a pipe or tube through which the flow of fluid and pupae may travel. At the inlet 114, the primary channel 118 includes a funnel 116 which reduces the size of the primary channel 118 from the size of the inlet 114. After the funnel 116, the primary channel 118 may have a width or height corresponding to a size of insect pupae (or other juvenile insects) intended to be isolated by the isolation device 100. The estimated size of the insect pupae may be a dimension such as a maximum expected width or height of a representative insect pupa or an average expected size. In some examples, the size may be based on a maximum expected cross-sectional area or a cross-sectional dimension based on a width and height of the insect pupa. The size may also refer to a width of the cephalothorax or length of the pupa. In some examples, the primary channel 118 may have a cross-sectional dimension corresponding to a size of the pupae including a width and height, each sized according to an anticipated size or diameter of the pupae. For example, in the case of mosquitoes, the primary channel 118 may have a width or height of around 1 to 2 mm. In some examples, the primary channel 118 may have a width of around 1.2 mm. For other insects or objects to be isolated by the isolation device 100, the size of the primary channel 118 may be selected based on the expected sizes of such other insects or objects. The primary channel 118 should be sized, meaning have a width, a height, a cross-section, etc., such that only a single insect pupae can be at any location along the primary channel 118 at any one point in time, e.g. two such insect pupae cannot fit side-by-side in the primary channel 118 after the funnel 116. Thus, the primary channel 118 should have a width. height, cross-section near the expected or anticipated size of insect pupae to be isolated.

The primary channel 118 has a constant width and height and therefore, as additional fluid is added by the secondary channels 122, the flow rate within the primary channel 118 downstream of each intersection 124 is higher than the flow rate of the section previous to it. In some examples, this difference in speed may be used to isolate or separate individual pupae. In other examples, the primary channel 118 may have a variable size, such as a diameter or width that increases further downstream nearer the outlet 112, which may then reduce the speed of the fluid within the primary channel 118. The primary channel 118 may be narrowed, or widened at different stages, for example near the outlet 112 to adjust the flow velocity within primary channel 118.

Downstream of the inlet 114 and the funnel 116, the primary channel 118 is intersected by a secondary channel 122a at an intersection 124a. As shown in the figures, the intersection includes the primary channel 118 and secondary channel 122a meeting at a perpendicular angle. In some examples, the intersection may be angled such that secondary channel 120a and the downstream portion of primary channel 118 form an obtuse angle. In other words, secondary channel 122a is angled or directed toward outlet 112. In some cases, the intersection may be formed by secondary channel 120a and primary channel 118 forming an acute angle. Further, additional secondary channels may be employed in some examples. In the example shown in FIG. 1, there are seven secondary channels 122a-g that intersect the primary channel 118 along the length of the primary channel 118. Each secondary channel 122a-g is fed by an inlet 120a-g. The inlets 120a-g connect to one or more fluid sources which provide a fluid flow into the primary channel 118 via the secondary channels 122a-g. Each of the secondary channels 122a-g is sized smaller than the expected pupae size. For example, the secondary channel 122a-g may have a height or width of less than 1 mm. This ensures that the insects are not able to enter the secondary channels 122a-g because they are larger than the opening or at least one dimension of the secondary channels 122a-g. In some examples, the secondary channel 122a-g may have similar dimensions to the primary channel 118. Downstream of the last secondary channel 122g, the primary channel 118 exits the isolation device 100 at the outlet 112.

In use, the isolation device 100 includes a first fluid flow traveling into the isolation device 100 at the inlet 114 and one or more second fluid flows traveling or entering the isolation device 100 at each respective inlet 120a-g of the secondary channels 122a-g. The second fluid flows intersect the first fluid flow and the combined flow exits the isolation device 100 at the outlet 112. As one or more pupae enter the isolation device 100, the funnel 116 guides the pupae from the inlet 114 into the primary channel 118. As a first pupae passes each of the secondary channels 122a-g, the respective second fluid flow introduces additional fluid into the first fluid flow, resulting in additional spacing or distance between adjacent pupae. For example, when two pupae enter the primary channel 118 adjacent each other, potentially even in contact with each other, the second fluid flow coming from the secondary channel 122a-g adds fluid into the primary channel 118 and this added fluid, thereby increasing the speed of the first pupa, but the second, thereby separating the first pupa and the second pupa within the primary channel 118.

When a first pupa enters the isolation device 100 at the inlet 114, the funnel 116 ensures that the first pupa, as well as any additional pupae, enter the primary channel 118 one at a time. The first pupa advances downstream along the primary channel 118 passing the intersections 124a-g. At each intersection 124a-g, fluid added by the secondary channels 122a-g increases a gap or space in between the first pupa and additional pupae as discussed above. In some examples, after a pupa passes a last intersection 124g, a sensor such as a light curtain or optical sensor detects the pupa passing the intersection and in response, a processor causes the outlet 112 to close. With the outlet 112 shut, the first pupa remains stagnant while the additional fluid entering through the secondary channels 122a-g reverses course and flows upstream towards the inlet 114, carrying the additional insect pupae upstream as well. Meanwhile, the first insect pupae may be observed or imaged through the clear glass plate for classification and sorting.

Figure 2:
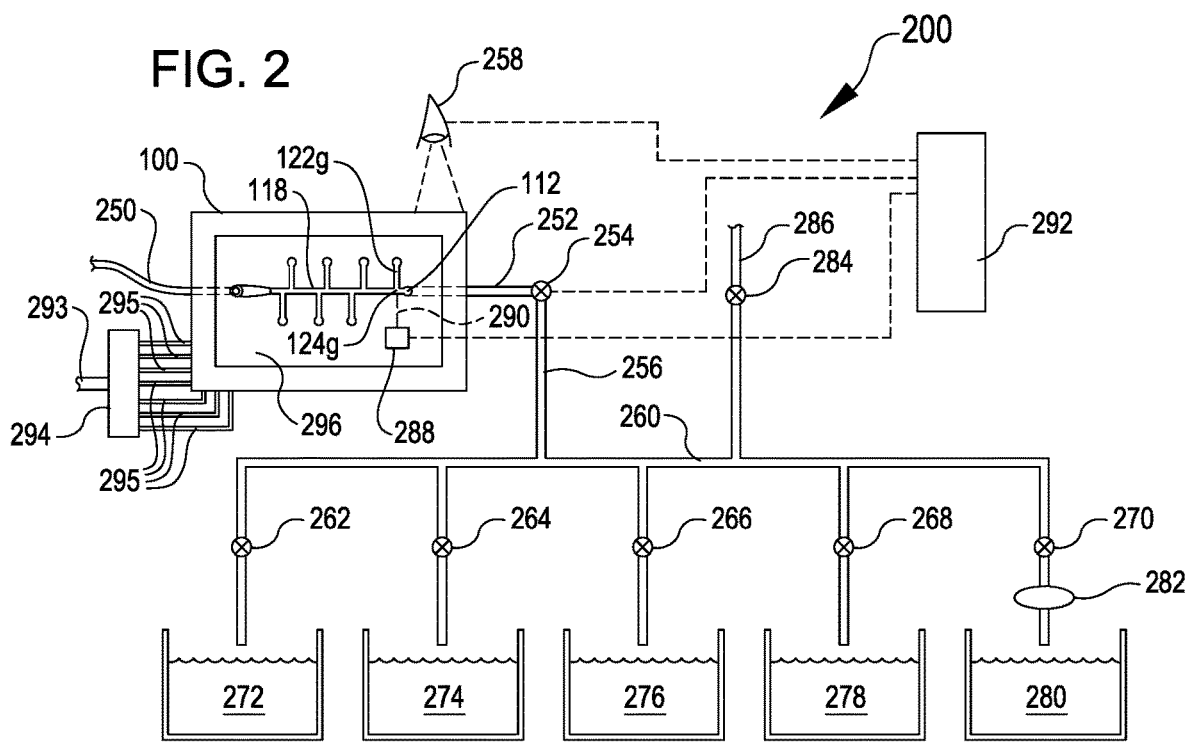
FIG. 2 illustrates a sorting system for insect pupae, according to at least one example.

In some examples, the space created between the first pupa and additional pupae may be sufficient to capture an image or observe the first pupa to determine a characteristic by which the pupae are being sorted without closing the outlet 112 and stopping the fluid flow through the outlet. In some other examples, the outlet 112 may be partially closed to slow the progress of the pupae along the primary channel 118 sufficiently to observe or capture an image or other data concerning the pupae for sorting before returning to normal speed. Such a system would use a pupae detection system, as described herein, to detect when a pupa enters a data gathering zone (as shown in FIG. 2 located underneath optical sensor 258), such as an area within or underneath a viewport or clear viewing plate. When a pupa is in the data gathering zone, the outlet 112 may be partially closed to slow the pupa until the data is gathered, at which point the outlet 112 may be opened until a new pupa enters the data gathering zone.

As the insect pupae advance along the primary channel 118, they may separate from each other due to differences in speed between different regions of the isolation device 100. In at least one additional example, a first insect pupa enters the isolation device 100 at the inlet 114 and advances along the primary channel 118. Additional insect pupae may also enter the isolation device 100 following or at around the same time as the first insect pupa and also enter the primary channel 118. The funnel 116, as well as the size of the primary channel 118 (which is only large enough for a single insect pupa to fit at any location along the length in this example) ensures that the insect pupae enter the primary channel 118 one after another. The first insect pupa may pass the first four intersections 124a-d and corresponding secondary channels 122a-d. The outlet 112 may be shut, either as a result of a pupae detection system positioned along the primary channel 118 or based on observation of the pupa in the primary channel 118. At around or at the same time the outlet 112 is shut, the inlets 120e-g corresponding to the secondary channels 122e-g may also be shut such that fluid flow beyond intersection 124d ceases and the fluid, with the first insect pupa, remains stagnant. The additional insect pupae, which are positioned along the length of the primary channel 118, but have not yet reached intersection 124d, are then pushed back upstream towards the inlet 114 by the fluid flows from the secondary channels 122a-d, which are still active. The first pupa is thereby isolated and prepared for imaging, identification, or any other process which requires singulation or isolation of the insect pupa.

The isolation device 100 may also be configured to prevent clogs from obstructing flow along the primary channel 118. The funnel 116 helps ensure that insect pupae enter the primary channel 118 one at a time, but in some instances, material, foreign objects, or over-sized pupae may enter the inlet 114 and block or partially block the primary channel 118. Closing the outlet 112 results in the flow from the secondary channels 122a-g flowing in the opposite direction of the first flow, heading from the outlet 112 towards the inlet 114. As a result, when a blockage is observed or detected by an optical sensor, technician, or pressure sensor in the system, the outlet 112 may be temporarily shut to backflush the clog or blockage before re-opening to resume normal operation. For example, an optical sensor may observe that insect pupae have ceased advancing along primary channel 118 and a technician or computing device may be alerted to either manually or automatically shut outlet 112 to backflush primary channel 118.

In some examples, the isolation device 100 may include only one secondary channel intersecting the primary channel 118 between the inlet 114 and the outlet 112. In some other examples, additional secondary channels may be included to introduce additional second fluid flows and thereby provide greater or additional separation or distance between adjacent pupae, such as described above with respect to FIG. 1.

When the outlet 112 is closed, the first fluid flow ceases to advance within the primary channel 118 along from the inlet 114 to the outlet 112 because the outlet 112 is closed and there is not alternative exit for the first fluid flow. The second fluid flow entering through the secondary channels 122a-g continues to flow but after intersecting the primary channel 118, the second fluid flow backflows along the primary channel 118 towards the inlet 114. The backflow flushes any object, insect pupae or otherwise, which had been carried into the primary channel 118 by the first fluid flow and pushes them back towards or out the inlet 114. Any insect pupae or objects which have traversed the intersection 124g of the last, or furthest downstream, secondary channel 122g, is not pushed back towards the inlet 114, but instead remains within the primary channel 118 near the outlet 112. This provides an opportunity to observe, image, view, or perform operations on the pupa which is stationary near the outlet 112.

The flow rate of the first fluid flow may vary, depending on the intended use of the isolation device 100, however, as described below, some automated uses of the isolation device 100 may enable flow rates in a range of between ten mL/min and one thousand mL/min. In some instances, the flow rates may be in a range of 160 mL/min to 300 mL/min. The flow rate of water through inlet 114 may differ from the flow rate through secondary channels 122a-g. Having a higher ratio of water flowing through the secondary channels 122a-g compared to water flowing through inlet 114 helps ensure that pupae are adequately separated in the isolation device 100. The first fluid flow rate may vary during operation or be set during an setup stage. Likewise, the flow rate of the second fluid flows may be variable and adjusted either during setup or vary during operation.

FIG. 2 illustrates an example sorting system 200 for implementing the isolation device 100 of FIG. 1 in a system for sorting insects in a fluid or aqueous solution, according to at least one example. The system includes a computer system 292, such as described in FIG. 5 below which may be used to perform operations or processes described herein using system 200. The computer system 292 is shown in communication with optical sensor 258, pupae detection system 288, and valve 254, though it may also be in communication with other elements of the system such as other valves, manifold 294, diaphragm 282, or other system elements. The aqueous solution enters the system through a delivery tube 250 from a storage container, holding tank, or other storage or solution transport device. The delivery tube 250 is in fluid communication with the inlet 114 of the isolation device 100. A second delivery tube (not shown) provides the second fluid flow to the secondary channels 122a-g through inlets 120a-g. As a flow of fluid and pupae enter the primary channel 118, the funnel 116 helps ensure that the pupae enter the primary channel 118 one at a time. As the pupae pass the secondary channels 122a-g, the second fluid flow is added into the first fluid flow to separate adjacent pupae in the primary channel 118 as they travel downstream from the inlet 114 to the outlet 112.

Each of the inlets 120a-g is fed a flow of fluid separate and distinct from the first flow of fluid. The inlets 120a-g may include valves to selectively open, close, or reduce a flow of fluid through each inlet 120a-g. In some examples, a manifold 294 may receive a flow of fluid from tube 293 and provide fluid connections 295 to each inlet 120a-g. The manifold 294 may be capable of selectively shutting off fluid flow to any or all of the inlets 120a-g. In use, when a first insect pupa is within the isolation device 100, when the outlet 112 is shut, stopping the forward primary fluid flow, the additional flow to any of the inlets 120a-g may be simultaneously shut off as described above with respect to FIG. 1.

Downstream or at the intersection 124g of the last or most downstream secondary channel 122g with the primary channel 118 is a pupae detection system 288. In FIG. 2, the pupae detection system 288 is shown as including an optical detection device, such as a laser gate or light curtain which projects a light beam 290 onto a light sensor, e.g., a photodetector. The pupae detection system 288 detects a pupa traversing the intersection 124g when the light beam 290 is blocked by the pupa. Other pupa detection devices 288 are contemplated including optical eyes, cameras, laser gates, light curtains, and other such detection devices capable of detecting a presence of a physical object within the primary channel 118. In some instances, the pupa may be detected by visual observation by an individual operating the system 200.

When the pupa detection device 288 detects or determines that a single pupa has passed the last or furthest downstream intersection 124g of the primary channel 118 and the secondary channel 122g, the computing device 292 may output a signal to close a valve 254, and the outlet 112 of the isolation device 100 may be shut. Closing the outlet 112 causes the second flow to backflush additional pupae from the primary channel 118 as described above, e.g., toward the inlet 114. This process positions the single pupa for viewing or for classifying the pupa by insect type. Determining the insect type may include a sex determination, such as male or female, it may also include pupal or larval stage determination or identification of foreign non-insect objects. In some examples, the object viewed while in the isolation device 100 may be identified using object recognition techniques or image recognition techniques. The insect type may also be determined based on size or other identifying factors as described above, including antennae, sex organs, tail shape or size, or other characteristics.

As shown in FIG. 2, an optical sensor 258, such as a camera, may be positioned above the isolation device 100 and aimed to observe the insect pupae through a cover 296 which is transparent. In some examples, the cover 296 may have a transparent viewport or transparent portion through which the optical sensor may be directed. Further, in some examples, an underside of the separation device 100 may be transparent and allow the sensor to be positioned beneath the separation device 100.

The optical sensor 258 may include any suitable combination of image sensors, lenses, computer hardware, or software, may be in network communication with a computing system (not shown). In some other examples, the optical sensor 258 may be positioned at or adjacent to the outlet 112 of the isolation device 100 or positioned after the outlet 112, for example at the exit tube 252. The exit tube 252 in the particular example shown in FIG. 2 may be formed of a clear or transparent material or include a viewing window to view the pupa. The outlet 112 may be closed by a closing device such as a valve, stopper, deflection plate, or other shutoff device. The valve 254 may control the opening and closing action of the outlet 112. In some instances, the valve 254 may be positioned at or adjacent to the isolation device 100, while in other examples, the valve 254 may be removed or separated from the isolation device 100 by any suitable distance.

The pupa/insect may be sorted by a system of valves and tubes or delivery conduits. For example, a pupa may pass the optical sensor 258 in conduit 256 and be delivered into one of several containment systems 272, 274, 276, 278, and 280 when computer 292 sends a signal to selectively open and close valves 262, 264, 266, 268, or 270, based on the insect type determination made earlier. In at least one example, the containment systems 272, 274, 276, 278, and 280 may include containers for male pupae, female pupae, larvae, adult insects, or waste, among other possible identifiers. In some examples, particularly for a SIT program, only male mosquitoes may be desired, so the system 200 may include a container system 272 for male pupae with the remainder of the objects coming through the isolation device routed into a waste container or disposal. Corresponding valves, 262, 264, 266, 268, and 270 may be opened or closed based on a location a particular insect/pupae/object is to be routed. And while five containment systems 272-280 are depicted, any suitable number may be employed, along with a corresponding system of valves and tubing.

The system 200 includes an inlet 286 and control valve 284 for providing fluid to flush the sorting system 200 and drive a pupa or object into a desired branch or container system 272, 274, 276, 278, and 280. After an individual insect or pupa is isolated by the isolation device 100, the system 200 may include elements to adjust the position and or location of the insect/pupa through the use of a diaphragm 282 in concert with the inlet 286. Diaphragm 282 may include a fluid line 283 and valve 270 to control flow of fluid through fluid line 283. Increasing fluid or pressure on one side of diaphragm 282 pushes diaphragm 282 or flexes a deformable portion of diaphragm 282 to displace liquid within sorting system 200. The diaphragm 282 may be used to add or release pressure from the system 200 to finely position or adjust a position of an object, particularly around the optical sensor 258. In some examples, the diaphragm 282 may be replaced by a fluid inlet and control valve.

Each of the elements of the system 200, including the valves 254, 262, 264, 266, 268, 270, and 284, manifold 294, the pupa detection device 288, the optical sensor 258, and the diaphragm 282, may be in communication with a computer system 292. In this example, each valve 254, 262, 264, 266, 268, 270, and 284 may be actuated by an appropriate signal sent by the computer system, e.g., a logical '0' or '1' to fully open or close the corresponding valve, by sending an analog voltage to set any desired position between (and including) fully open and fully closed, etc. The computer system 292, as described herein, is any suitable electronic device (e.g., personal computer, hand-held device, server computer, server cluster, virtual computer, etc.) configured to execute computer-executable instructions to perform operations such as those described herein. As described in additional detail with respect to FIGS. 3, 4, and 5, the computer system can include a processor configured to operate one or more sorting modules, among other modules/components, and includes the functionality to perform the processes described herein.

Figure 6:
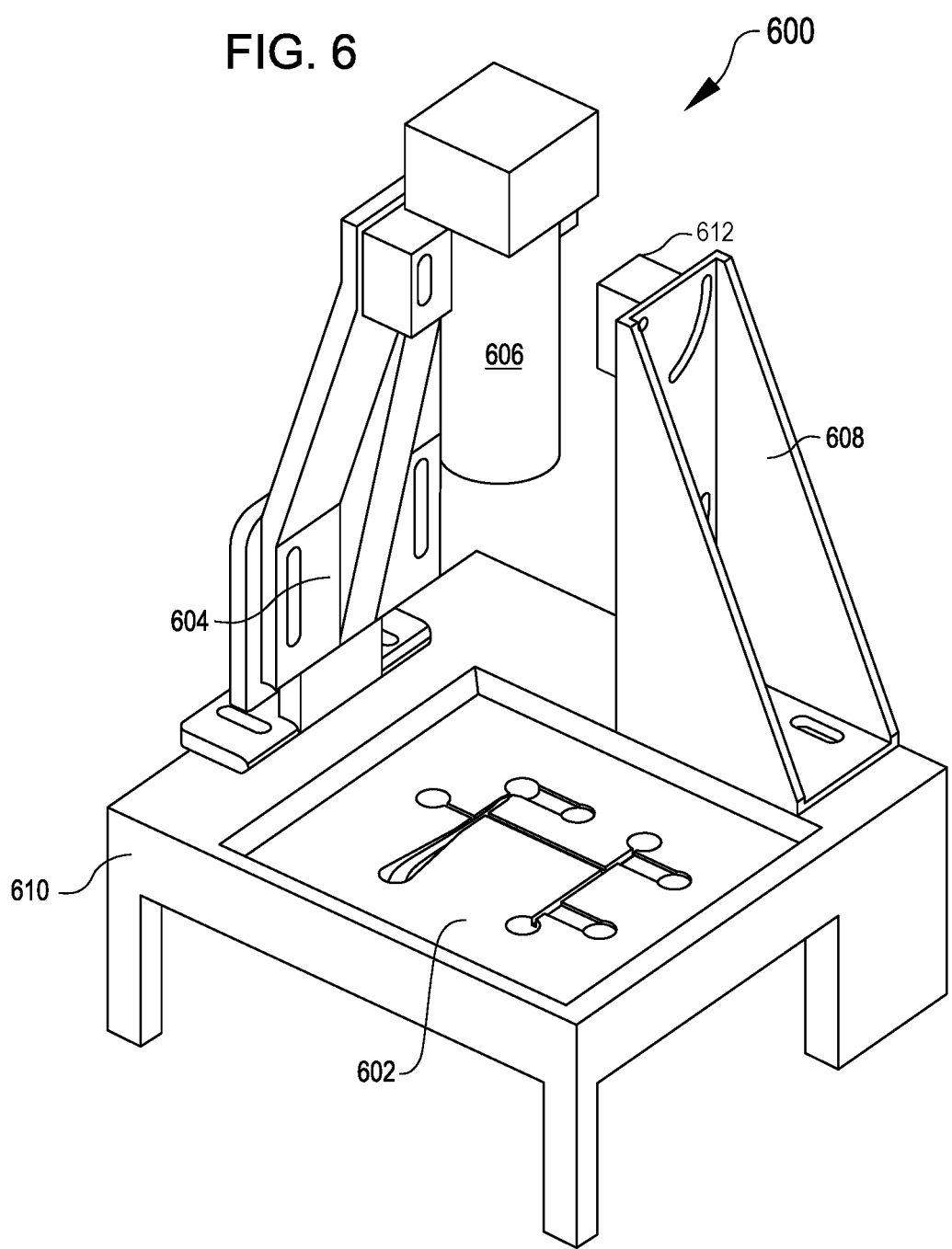
FIG. 6 illustrates an imaging and sorting system for insect pupae, according to at least one example.

FIG. 6 illustrates an imaging and sorting system 600 for insect pupae, according to at least one example. The imaging and sorting system 600 includes an isolation device 602, base 610, optical sensor 606, optical sensor mount 604, sensor mount 608, and sensor 612. The system may also include a computer system, such as computer system 292, as well as actuatable valves and storage containers, as described with respect to FIG. 2. The computer system is in communication with valves, such as valves connected to inlets and outlets of the isolation device 602 to enable isolation of insect pupae in the isolation device as well as with the optical sensor 606 to enable image capture of the insect pupae. The imaging and sorting system 600 may be incorporated with other system elements of sorting system 200 such as the manifold 294, and containment systems 272, 274, 276, 278, and 280. In some examples, the imaging and sorting system 600 may be an example of the isolation device 100 and optical sensor 258.

The isolation device 602 may be isolation device 100 described above with respect to FIGS. 1-2 or may have a different structure that enables isolation of insect pupae from a liquid flow and sorting into various storage containers. The example of isolation device 602 of FIG. 6 is described with respect to FIG. 7 below. The isolation device 602 is maintained in position by the base 610 and may be removable or interchangeable, for example to replace with isolation device 100.

Base 610 additionally supports optical sensor mount 604 and sensor mount 608. Optical sensor mount 604 maintains optical sensor 606 in position over the isolation device 602 to capture images of insect pupae isolated within the isolation device 602. The optical sensor 606 is positioned above an isolation or imaging portion of the isolation device 602, where insect pupae can be maintained, temporarily, in position for imaging before being directed, using liquid flows, through an outlet of the isolation device 602 for storage in a storage system. The optical sensor 606 may include any suitable combination of image sensors, lenses, computer hardware, or software, may be in network communication with a computing system (not shown). In some examples, the isolation device 602 may be formed of a transparent material such that images may be captures of an insect pupae from multiple angles, in such examples, optical sensor mount 604 may support more than one optical sensor, such as with a first optical sensor above the isolation device with a second optical sensor below the isolation device. In some examples additional optical sensors may be positioned at an angle other than perpendicular with respect to the surface of the isolation device 602.

The sensor mount 608 supports a sensor 612 that may gather additional data regarding the presence of insects within the isolation device 602. For example, the sensor may include an optical sensor that detects when an insect pupae is within an imaging section of the isolation device 602 or may be associated with a counter to maintain a count of insect pupae sorted through each outlet of the isolation device 602. The sensor 612 may include any number of physical or optical sensors including laser gates, optical sensors, contact sensors, deflection sensors, or other such sensors capable of detecting the presence or passage of insect pupae through a channel of the isolation device 602.

Figure 7:
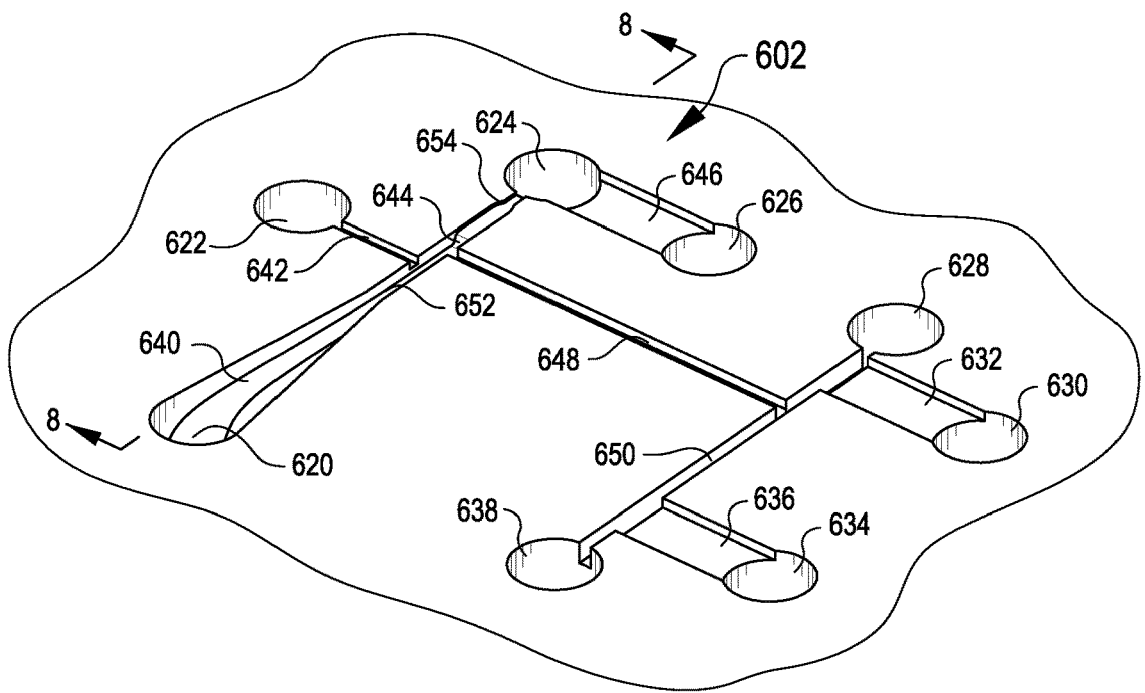
FIG. 7 illustrates an isolation device of the imaging and sorting system of FIG. 6, according to at least one example.

FIG. 7 illustrates an isolation device 602 of the imaging and sorting system 600 of FIG. 6, according to at least one example. The isolation device 602 illustrates a second example of a configuration of the isolation device 100 and may be interchangeable with the isolation device 100 in various systems.

The isolation device 602 includes an insect pupae inlet 620, first channel 652, second channel 648, third channel 650, liquid inlets 622, 626, 630, and 634, and liquid outlets 624, 628, and 638. Additional features of the isolation device 602 enable introduction of insect pupae, isolation of the insect pupae from a plurality of insect pupae, imaging of the insect pupae, and sorting of the insect pupae through different outlets based on different characteristics of the insect pupae determined based on the imaging of the insect pupae.

Insect pupae inlet 620 enables a flow of liquid and insect pupae to enter the isolation device 602 from a storage unit including liquid and a plurality of insect pupae. A funnel 640 guides insect pupae from the insect pupae inlet 620 into a first channel 652. The first channel is intersected by a second channel 648 and a fourth channel 642 and includes a liquid inlet 626 and a liquid outlet 624 at an end of the first channel 652 opposite the insect pupae inlet 620. The fourth channel 642 and liquid inlet 622 enable introduction of a second flow of liquid into the first channel 652 to isolate an insect pupae from a plurality of insect pupae as described with respect to the primary channel 118 and secondary channel 122 of FIG. 1. Further, the liquid inlet 626 and liquid outlet 624 enable selective introduction and removal of liquid from the first channel 652 to enable fine positioning of an insect pupae that has passed the fourth channel 642. The fourth channel 642 may have a dimension smaller than a width of a representative insect pupae to prevent insect pupae from entering the fourth channel 642.

At the end of the first channel 652 opposite the insect pupae inlet 620, are a first constriction 644, a second constriction, liquid inlet 626, and liquid outlet 624. The liquid inlet 626 and liquid outlet are useful for introducing and removing liquid from the first channel 652 to position the insect pupae within the first channel 652 at a position suitable for imaging with the optical device 606. The liquid inlet 626 is connected to the first channel through shallow passage 646. The shallow passage 646 enables liquid to flow from liquid inlet 626 to the first channel 652 to push or displace insect pupae away from first constriction 644, back towards insect pupae inlet 620. The shallow passage 626 has a width greater than the width of the first channel 652 such that the volumetric flow rate of liquid is not restricted through a narrow and shallow channel. The shallow passage 646 enables liquid from liquid inlet 626 to cause insect pupae to move upstream from the first constriction 644 for redirection into second channel 648 for sorting. The first constriction 644 and the second constriction 654 narrow the depth and width of the first channel 652 to aid in positioning insect pupae as well as to prevent insect pupae from passing beyond the second constriction 654 to the liquid inlet 626 and liquid outlet 624. The first constriction 644 and second constriction 654 are shown and described with further detail with respect to FIG. 8.

The second channel 648 intersects the first channel 652 downstream of the fourth channel 642. This positioning enables the isolation device 602 to isolate an individual insect pupae downstream of the fourth channel 642 and subsequently image the insect pupae and direct the insect pupae through the second channel 648 for sorting through outlet 628 or 638. The second channel 648 has a cross sectional area and dimensions similar to, or in some cases identical to, the dimensions and cross sectional area of the first channel 652. In some examples, the second channel 648 may have a smaller width or depth than the first channel such that flow through the second channel 648 is faster than flow through the first channel 652.

At the end of the second channel 648 opposite the first channel 652, the second channel 648 intersects a third channel 650. The third channel 650 has the same width and depth as the second channel 648. In some examples, the width and depth of the third channel 650 may be greater than or less than the width of the first channel 652 or the second channel 648. At opposite ends of the third channel 650 are inlets 630, 634 and outlets 628, 638. The dimensions of third channel 650 may be adjusted to bias the flow of liquid through the channel, for example by ensuring that unintended objects that flow through the third channel 650 proceed to outlet 638, which may be a reject outlet that goes to a disposal system. The bias within the third channel may be accomplished by varying a distance between the second channel 648 and the outlets 628, 638, such that a distance between outlet 638 and the second channel 648 is greater than a distance between outlet 628 and the second channel 648. Additionally, constrictions may be positioned within the third channel 650, for example between wide shallow channel 632 and outlet 628 to reduce a fluid flow in the direction of outlet 628. The inlets 630, 634 are connected to the third channel 650 via wide shallow channels 632, 636 similar to the shallow channel 646. In some examples, the wide shallow channels 632, 636 may have different dimensions from the shallow channel 646. The shallow channel prevents insect pupae from traveling up the liquid inlets 630, 634. Liquid inlets 630, 634 enable liquid to be introduced into the third channel to drive or carry an insect pupae through the third channel 650 to an outlet 628, 638 based on the type of insect pupae or a desired destination. The outlets 628, 638 each connect, via a valve and conduit, to a storage system for insect pupae. The storage system may include a first storage unit for a first type of insect pupae and a second storage unit for a second type of insect pupae, such as a male insect pupae and a female insect pupae. As described herein, the various inlets and outlets of the isolation device 602 are each coupled to closeable valves that selectively enable or restrict flow through the various inlets and outlets as controlled to route insect pupae for imaging and subsequent sorting.

In some examples, the isolation device 602 may include one or more physical actuators that actuate to block one or more portions of the channels of the isolation device 602. For example, mechanical actuators may be positioned in or adjacent the fourth channel 642 to selectively actuate and enable or restrict flow through the fourth channel based on the position of the actuator. Similar actuators may be positioned within the first channel 652 adjacent the inlet 624 or at the intersection of the first channel 652 and the fourth channel 642. In some examples the second channel 648 and third channel 650 may likewise include similar actuators to alter or change flow directions within the isolation device 602.

Figure 8:
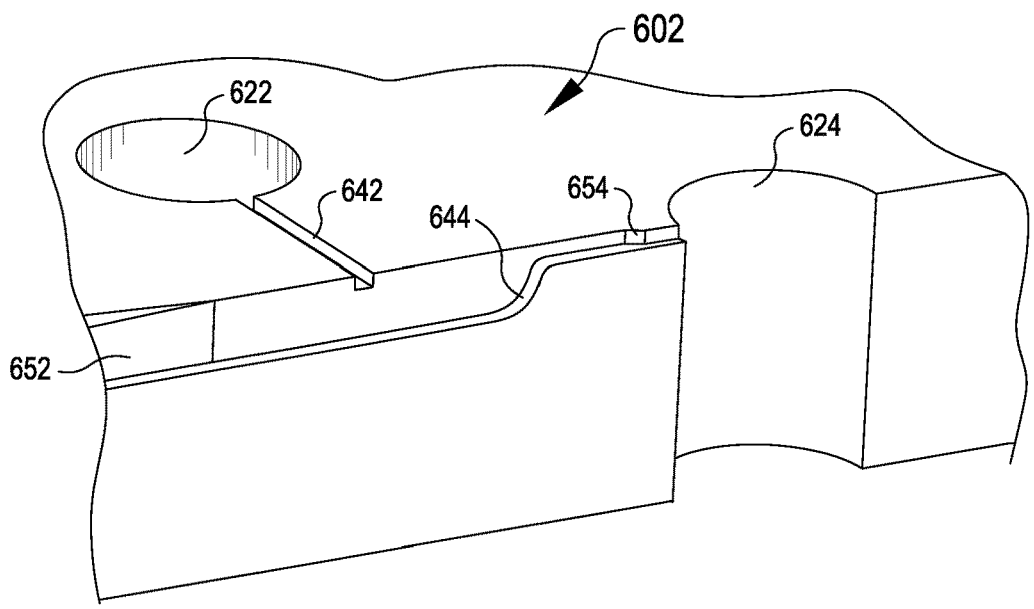
FIG. 8 illustrates a section view of the isolation device of FIG. 7 showing a first channel of the isolation device, according to at least one example.
Figure 9:
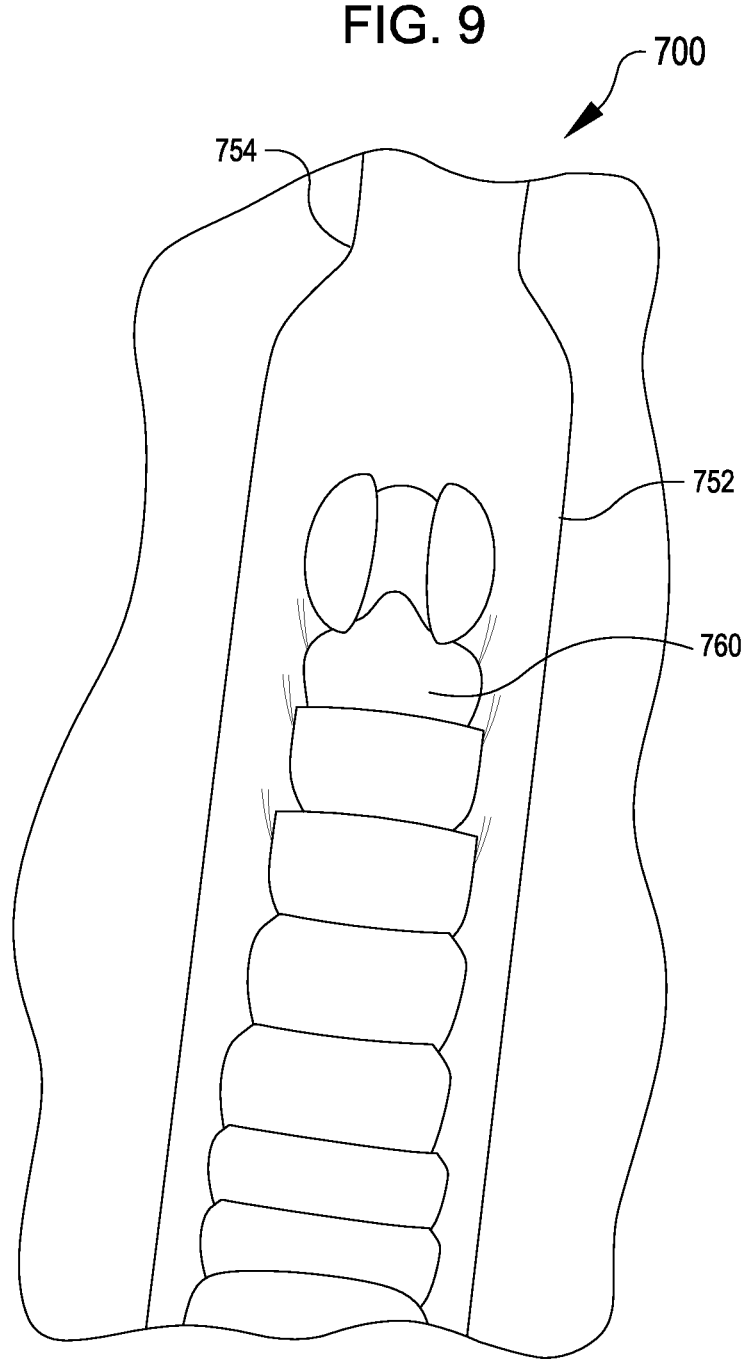
FIG. 9 illustrates an example image of a portion of an insect pupae captured using the imaging and sorting system of FIG. 6, according to at least one example.

FIG. 8 illustrates a section view of the isolation device of FIG. 7 showing the first channel 652 of the isolation device 602, according to at least one example. In particular, the first constriction 644 and the second constriction 654 are shown in the section view. The first constriction 644 results in a second depth for the first channel 652, the second depth less than a first depth upstream of the first constriction 644. The second constriction 654 results in a second width, the second width less than a first width of the first channel 652. The second depth is has a dimension less than a widest portion of a representative insect pupa such that the tails of the insect pupae can pass the first constriction 644 however the second constriction 654 is sized such that the insect pupa cannot flow past. The first constriction 644 ensures the insect pupae are positioned at or near an upper surface of the isolation device 602 for imaging by the optical device 606. The second constriction 654 ensures the insect pupae is aligned along a length of the first channel 652 such that the tail of an insect pupae is parallel with an axis of the first channel 652, as illustrated in FIG. 9. Additionally, the first constriction 644 ensures that insect pupae cannot flow past the constrictions towards the inlet 624 or outlet 626 as only the insect pupae tail can pass the first constriction 644.

FIG. 9 illustrates an example image 700 of a portion of an insect pupae captured using the imaging and sorting system of FIG. 6, according to at least one example. The insect pupae is positioned within the first channel 752, which is the first channel 652 of FIGS. 6-8. The insect pupae tail 760 is aligned with the first channel 652. The insect pupae tail 760 may fit between the walls of the first channel 652 downstream of the second constriction 754, which may be the same as second constriction 654. In some examples, the second constriction 754 may enable only a portion of the insect pupae tail 760 to pass the second constriction 754, while a thorax or other portion of the insect pupae has a width greater than the width of the second constriction 754. In such examples, the insect pupae tail 760 may be sufficiently stable and still for proper imaging by the optical device 606. The image is captured by the optical device 606 for use in classifying the insect pupae and the insect pupae is subsequently directed through the channels of the isolation device based on the classification of the insect pupae.

Figure 3:
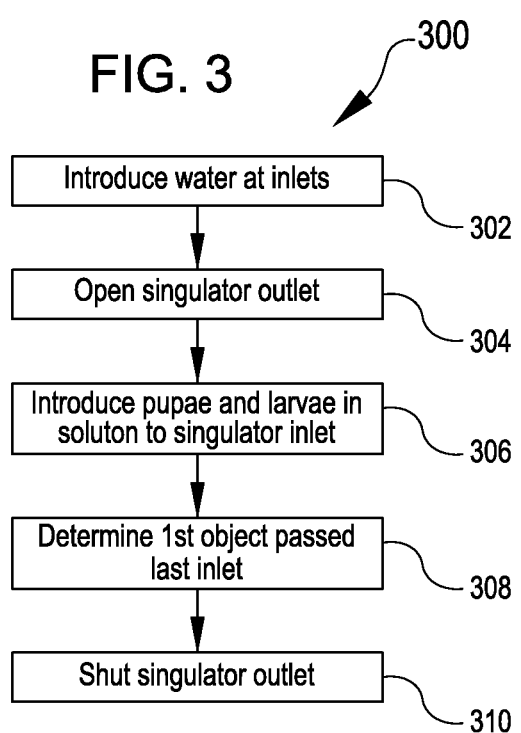
FIG. 3 illustrates an example process for isolating individual insect pupae, according to at least one example.

FIG. 3 illustrates an example process 300 for isolating a single insect within a flow of aqueous solution including insect pupae, according to at least one example. The process 300 for sorting is described with respect to the system shown in FIG. 2, though it should be appreciated that any suitable system according to this disclosure may be employed. In the process 300, at block 302, a first fluid is introduced at an inlet 114 of a primary channel 118 of an isolation device 100. The first fluid flows from the inlet 114 to an outlet 112 of the primary channel 118. Additionally, at block 302, a second fluid is introduced into the isolation device 100 through a secondary channel 122. Each secondary channel 122*a-g* intersects the primary channel 118 and delivers the second fluid into the primary channel 118. In some examples, the process 300 may further include introducing additional fluid flows through additional secondary channels 122. Outlet 112 is opened at block 304, allowing fluid to flow through primary channel 118 and through the system 200.

As the insects are introduced into the first fluid and the isolation device 100 at block 306, they are guided into the primary channel 118 by a funnel 116 and or shaped walls to transition from the inlet 114 into the primary channel 118, traveling in a first direction towards the outlet 112 of the primary channel 118. As the insects pass the intersections 124*a-g* of the primary channel 118 and the secondary channels 122*a-g*, the second fluid flows from the secondary channels 122*a-g* increases the flow volume within the primary channel 118 which results in the pupae traveling faster down the primary channel 118 once they pass through the intersections 124*a-g* with the secondary channels 122*a-g*.

The result of the increase in speed is a distance or space created between a first insect and a second insect.

At block 308 of the process 300, the computer 292 receives a sensor signal from the sensor 258 and determines, based on the sensor signal, that a first insect pupa has passed the intersection 124g of the furthest downstream secondary channel 122g and the primary channel 118. For example, the sensor 258 may include a light emitter and a corresponding light detector. When the light detector outputs a signal indicating that it is not receiving light from the light emitter, the computer 292 may determine that a first insect pupa has passed the intersection 124g.

In response to detecting the first insect pupa has passed the intersection 124g in block 308, at block 310 of the process 300, the computing device 292 outputs a signal to close the outlet 112 of the isolation device 100. In this example the computing device outputs a signal to close valve 254 to close the outlet 112. When the outlet 112 is shut, the first fluid flow will cease advancing in the first direction. The second fluid flow will continue to enter at the respective secondary channel 122a-g but upon entering the primary channel 118, the second fluid flow will proceed in a second direction, different from the first direction, i.e., toward the inlet 114. Thus, the second fluid flow will proceed from the intersection 124g of the primary channel 118 and the secondary channel 122g upstream towards the inlet 114. The second fluid flow will push other material, insects, and objects towards the inlet 114 while the outlet 112 is shut. Any objects, fluid, or insect pupae that have passed the intersection 124g of the secondary channel 122g and the primary channel 118 will remain in place and unaffected by the changing direction of flow. In some examples, these insect pupae, fluid, or objects are held suspended and stationary at a location near the outlet 112. While stationary, the insects or objects may be viewed, analyzed, classified, or otherwise observed as described above with respect to FIG. 2. The outlet 112 may be used to hold the insect pupae in place for imaging, and releasing a small amount of liquid through outlet 112 to isolate the pupa in a known, repeatable location each time for imaging.

Figure 4:
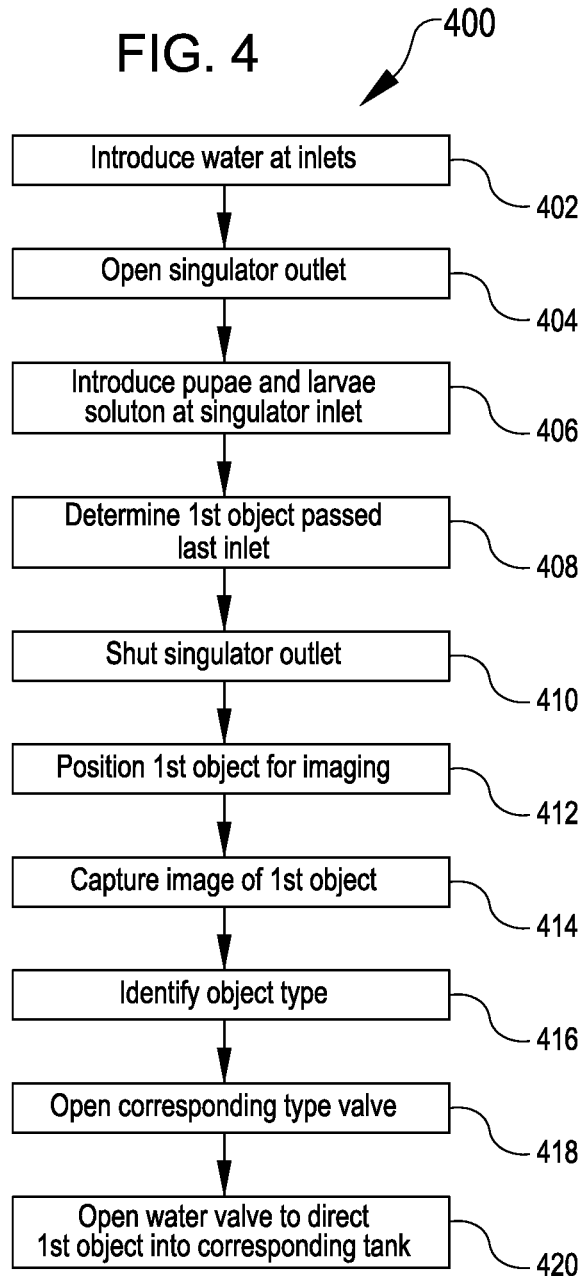
FIG. 4 illustrates an example process for classifying and sorting individual insect pupae, according to at least one example.

FIG. 4 illustrates an example process 400 for sorting insect pupae in an aqueous solution using an isolation device 100, according to at least one example. The process 400 may incorporate or use structures or devices described herein including the isolation device 100 described above as well as the sorting system 200. The process 400 for sorting may be implemented by a processor or a computer system as described above, in some examples the processes may also be performed by a human operator. Examples of the methods disclosed herein may be performed in the operation of such computer systems. The order of the blocks presented in the examples above can be varied—for example, blocks can be re-ordered, combined, or broken into sub-blocks. Certain blocks or processes can be performed in parallel.

In the process 400, at block 402, a first fluid is introduced at an inlet of a primary channel 118 of an isolation device 100, the fluid including insect pupae substantially as discussed above with respect to FIG. 3. The first fluid flows from an inlet 114 to an outlet 112 of the primary channel 118. At block 404, a second fluid flow is introduced into the isolation device 100 through one or more secondary channels 122a-g. Each secondary channel 122a-g intersects the primary channel 118 and delivers the second fluid into the primary channel 118 and the first fluid as discussed above. In some examples, the process 400 may further include providing additional secondary channels to deliver additional fluid flows into the primary channel 118 and therefore into the first fluid flow as well.

As the insects within the first fluid flow are introduced into the isolation device 100 at block 406, they are guided into the primary channel 118 by a funnel 116 generally as discussed above. As the singulated insects pass the first intersection 124a of the primary channel 118 and the first secondary channel 122a, the second fluid flow from the secondary channel 122a increases the flow volume within the primary channel 118 which results in the insect pupae traveling faster down the primary channel 118 once they pass through the intersection with the first secondary channel 122a. The result of the increase in speed is a distance or space created between a first insect and a second insect.

At block 408 of the process, a first insect pupa is determined to have passed the intersection 124g of the furthest downstream secondary channel 122g and the primary channel 118 generally as discussed above, such as with respect to block 308 of FIG. 3.

In response to detecting the first insect pupa has passed the intersection in block 408, at block 410 of the process 400, the outlet 112 of the isolation device 100 is shut generally as discussed above. Block 410 is the same as block 310 described above with respect to FIG. 3.

At block 412, the first insect pupae may be positioned for viewing or imaging. For example, when using an optical sensor 258 such as a camera, the insect may need to be positioned within a particular window for imaging. Using the diaphragm 282 or inlet 286 in concert with the valves 262, 264, 266, 268, and 270, the position of the insect may be finely adjusted for imaging. In particular, the diaphragm 282 may release or displace a portion of water within the system 200 to transport the insect downstream, by removing fluid or allowing the fluid to flow downstream through the system 200. In other instances, the diaphragm 282 may force fluid upstream within the system 200 to translate the insect upstream or backwards through the system 200. However, it should be appreciated that a diaphragm may not be employed in some examples. Instead, the pupae may be imaged as it moves through a region of the first channel, or the computing device 292 may receive a signal from the optical sensor 258 indicating that a pupa is in view and the computing device 292 may shut the outlet, or a corresponding valve, in response to such an indication. The outlet may be shut and alternately opened to release small amounts of liquid to finely adjust the location of the insect pupa for imaging as described above. In some examples, secondary channel 122g may be configured to allow liquid to flow towards or away from first channel 118 in order to adjust a position an insect pupae for imaging while outlet 112 is closed. For example, allowing liquid to flow from first channel 118 through secondary channel 122g and out inlet 120g moves an insect pupae upstream in channel 118, counter to the normal flow direction within channel 118.

At block 414, an image of the insect may be captured using an optical sensor 258 when imaging is used to classify the insects. In other examples, other classification methods may be used which require other data or information to be gathered from the isolated, positioned insect. Following the data gathering block 414, a computer system may identify an insect type at block 416 using any number of identifying techniques based on size or imaging. For example, a size or characteristic of a mosquito pupa may indicate whether the pupa is male or female.

After identifying an insect type, a valve associated with a sorting tank or destination corresponding to a trait by which the insect pupa is sorted is opened within the system 200 at block 418. For example, a first container system 272 may be provided for capturing male mosquito pupae, and a second container system 272 may be provided to capture anything else that travels through the system, e.g., female pupae, debris, etc. After a single pupa is isolated by the isolation device through blocks 402 through 410, the pupa may be identified as a male pupae, through characteristics identified in the image gathered of the pupae. Consequently, valve 262 is opened based on a signal output by computer 292 to allow the male pupa to travel to the container system 272. In some instances, the inlet 286 and valve 284 may be opened at block 420 to provide a fluid flow to enable the male pupae to travel to the container system 272, carried through the system 200 by the fluid flow.

FIG. 10 illustrates an example process 1000 for imaging and sorting insect pupae, according to at least one example. The example process 100 may include the imaging and sorting system 600, system 200, isolation device 100, or other systems described herein. The example process 100 for sorting insect pupae may include the process described above with respect to system 200 and imaging and sorting system 600, though it should be appreciated that any suitable system according to this disclosure may be employed.

In the process 1000, at block 1010, a flow of liquid is provided, the flow of liquid comprising pupae, into a first channel of an insect isolation unit. The flow of liquid is directed through the first channel in a first direction, the first channel having a dimension corresponding to a size of a representative pupa of the pupae. With reference to the isolation device 602, the first channel may be the first channel 652, with the flow of liquid introduced at the insect pupae inlet 620 and the first direction directed along the length of the first channel 652 away from the insect pupae inlet 620.

At block 1020, the process 1000 includes adjusting the flow of liquid to position an individual pupa in an imaging portion of the first channel. The flow of liquid may be adjusted by varying a flow rate through the insect pupae inlet 620, introducing a second flow through an additional channel, such as through fourth channel 642, introducing an additional flow through inlet 624, or varying an outlet rate through outlet 626 or any other outlet of the isolation device 602. The outlet rate may be varied by adjusting an open amount of a valve coupled to the outlet, for example with a variable valve that may be positioned at varying positions with varying percentages of open, such as fifty percent open. This may also include isolating the insect pupae within the first channel 652 as described with respect to process 300.

At block 1030, the process 1000 includes capturing an image of the individual pupa. The image is captured using the optical device 606 positioned over the isolation device 602. The image may include a portion of a tail of the insect pupa that is useful for identifying whether the insect pupa is male or female.

At block 1040, the process 1000 includes determining a pupa type of individual pupa based on the image captured by the optical device 606. The image may be processed by various algorithms including machine learning algorithms operated by a computing device to identify the characteristics of the insect pupa. The pupa type may be a male pupa, a female pupa, debris, or other such categories.

At block 1050, the process 1000 includes providing a second flow of fluid to sort the individual pupa into a first pupae outlet or a second pupae outlet based on the pupa type. The second flow of fluid directs the insect pupa through the outlets 628, 638 as described above. The second flow of fluid may be fluid that flows into the isolation device 602 through the insect pupae inlet 620 or any of inlets 624, 630, and 634. As described above with respect to block 418, the pupa may be directed through the outlet by selectively opening and closing valves to direct the insect pupa into an appropriate storage container based on the insect pupa characteristic.

Figure 5:
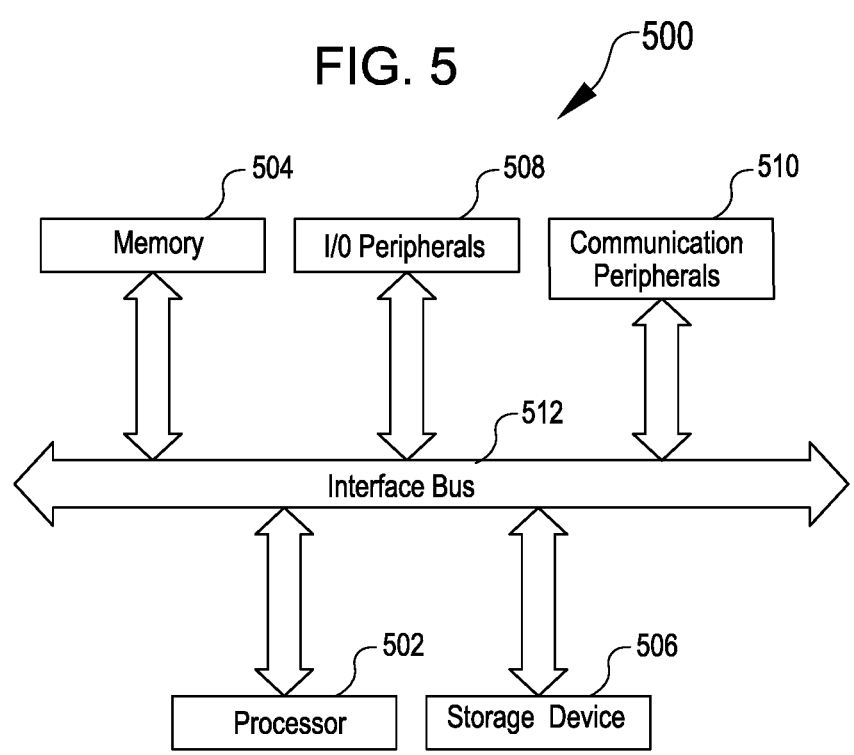
FIG. 5 illustrates an example computing system for use with systems and processes described herein.

FIG. 5 illustrates examples of components of a computer system 500, according to at least one example. The computer system 500 may be a single computer such as a user computing device or can represent a distributed computing system such as one or more server computing devices. The computer system 500 is an example of the computing device 292.

The computer system 500 may include at least a processor 502, a memory 504, a storage device 506, input/output peripherals (I/O) 508, communication peripherals 510, and an interface bus 512. The interface bus 512 is configured to communicate, transmit, and transfer data, controls, and commands among the various components of the computer system 500. The memory 504 and the storage device 506 include computer-readable storage media, such as Radom Access Memory (RAM), Read ROM, electrically erasable programmable read-only memory (EEPROM), hard drives, CD-ROMs, optical storage devices, magnetic storage devices, electronic non-volatile computer storage, for example Flash® memory, and other tangible storage media. Any of such computer-readable storage media can be configured to store instructions or program codes embodying aspects of the disclosure. The memory 504 and the storage device 506 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with the computer system 500.

Further, the memory 504 includes an operating system, programs, and applications. The processor 502 is configured to execute the stored instructions and includes, for example, a logical processing unit, a microprocessor, a digital signal processor, and other processors. The memory 504 or the processor 502 can be virtualized and can be hosted within another computing system of, for example, a cloud network or a data center. The I/O peripherals 508 include user interfaces, such as a keyboard, screen (e.g., a touch screen), microphone, speaker, other input/output devices, and computing components, such as graphical processing units, serial ports, parallel ports, universal serial buses, and other input/output peripherals. The I/O peripherals 508 are connected to the processor 502 through any of the ports coupled to the interface bus 512. The communication peripherals 510 are configured to facilitate communication between the computer system 500 and other computing devices over a communications network and include, for example, a network interface controller, modem, wireless and wired interface cards, antenna, and other communication peripherals.

While the present subject matter has been described in detail with respect to specific examples thereof, it will be appreciated that those skilled in the art, upon attaining an understanding of the foregoing may readily produce alterations to, variations of, and equivalents to such examples. Accordingly, it should be understood that the present disclosure has been presented for purposes of example rather than limitation, and does not preclude inclusion of such modifications, variations, or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more examples of the present subject matter. Any suitable programming, scripting, or other type of language or combinations of languages may be used to implement the teachings contained herein in software to be used in programming or configuring a computing device.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, or steps. Thus, such conditional language is not generally intended to imply that features, elements or steps are in any way required for one or more examples or that one or more examples necessarily include logic for deciding, with or without author input or prompting, whether these features, elements or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. An insect pupae sorting system, comprising:
    an isolation device comprising:
        a primary channel to deliver a first flow of liquid including insect pupae, the primary channel comprising an inlet and an outlet; and
        a first secondary channel that intersects the primary channel at a first intersection between the inlet and the outlet to deliver a second flow of liquid into the primary channel to generate a third flow of liquid and to separate adjacent insect pupae being transported through the primary channel;
    an optical sensor positioned proximate the outlet of the isolation device to capture images of pupae from the third flow of liquid, wherein the optical sensor is positioned between the first intersection and the outlet; and
    a storage unit system coupled to the outlet that includes a container into which insect pupae of a first type are directed based at least in part on the captured images.

2. The insect pupae sorting system of claim 1, wherein the storage unit system comprises:
    at least one container to support a volume of liquid and insect pupae; and
    a valve positioned on a conduit between the isolation device and the at least one container, wherein a single insect pupa that is separated from the adjacent insect pupae is directed into the at least one container by opening the valve.

3. The insect pupae sorting system of claim 1, wherein:
    the primary channel has a first cross-sectional dimension corresponding to a size of the insect pupae; and
    the first secondary channel has a second cross-sectional dimension smaller than a dimension of the insect pupae.

4. The insect pupae sorting system of claim 1, further comprising a pupa detection system for detecting when a single insect pupa passes the first intersection of the primary channel and the first secondary channel.

5. The insect pupae sorting system of claim 4, wherein the outlet comprises a closing device for shutting the outlet when the single insect pupa passes the first secondary channel.

6. The insect pupae sorting system of claim 4, wherein the optical sensor is configured to capture the image when the single insect pupa passes the first secondary channel.

7. The insect pupae sorting system of claim 1, wherein the isolation device further comprises a second secondary channel that intersects the primary channel between the first intersection and the outlet at a second intersection to selectively deliver a fourth flow of liquid into the primary channel to augment the third flow of liquid and to further separate the adjacent insect pupae being transported through the primary channel, wherein the second flow of liquid and the fourth flow of liquid are independently and selectively deliverable into the primary channel.

8. A method of sorting insect pupae, comprising:
providing, at an inlet of a primary channel of an insect isolation device, a flow of fluid comprising pupae in a first direction toward an outlet of the primary channel, the first primary channel having a dimension corresponding to a size of a representative pupa of the pupae;
providing, at a first intersection with the primary channel, a second flow of fluid through a first secondary channel into the primary channel;
determining that an individual pupa has passed the first secondary channel; and
after the individual pupa has passed the first secondary channel:
capturing an image of the individual pupa using an optical sensor positioned between the first intersection and the outlet;
determining a pupa type of the individual pupa based on the image; and
sorting the individual pupa based on the pupa type.

9. The method of claim 8, further comprising closing the outlet of the primary channel after the individual pupa has passed the first secondary channel, and wherein closing the outlet causes the flow of fluid to advance through the primary channel in a second direction, different from the first direction.

10. The method of claim 8, wherein sorting the individual pupa based on the pupa type comprises opening a valve downstream of the outlet of the primary channel to direct the individual pupa to a container system based on the pupa type.

11. The method of claim 8, further comprising determining a number of pupae sorted to each pupa type.

12. The method of claim 8, further comprising providing a third flow of fluid, through a second secondary channel, into the primary channel.

13. The method of claim 8, wherein determining that the individual pupa has passed the first secondary channel comprises using a laser gate across the primary channel adjacent to the first secondary channel.

14. The method of claim 8, wherein the pupa type is at least one of:
a male pupa;
a female pupa;
a larvae; or
debris.

15. An insect pupae sorting system, comprising:
an isolation device comprising:
a primary channel having an inlet and an outlet;
a first secondary channel intersecting the primary channel between the inlet and the outlet at a first intersection; and
a cover that encloses the primary channel and the first secondary channel into fully-enclosed passages;
an optical sensor positioned between the first intersection and the outlet to capture an image of an insect pupa in the isolation device;
a storage system including at least one holding tank in fluid communication with the isolation device; and
a processor configured to execute processor executable instructions stored in a non-transitory computer-readable medium configured to cause the processor to:
determine the insect pupa has passed the first secondary channel;
receive an image of the insect pupa from the optical sensor;
determine a pupa characteristic based on the image; and
cause the insect pupa to travel into holding tank of the storage system based at least in part on the pupa characteristic.

16. The insect pupae sorting system of claim 15, wherein the processor executable instructions are further configured to receive the image of the insect pupa when the insect pupa passes the first secondary channel.

17. The insect pupae sorting system of claim 16, wherein the processor executable instructions are further configured to cause the processor to cause the outlet to close after determining the insect pupa has passed the first secondary channel.

18. The insect pupae sorting system of claim 17, wherein the processor executable instructions are further configured to cause the processor to cause the outlet to open after capturing the image of the insect pupa.

19. The insect pupae sorting system of claim 15, wherein the pupa characteristic comprises at least one of:
male;
female;
larva; and
waste.

20. The insect pupae sorting system of claim 15, wherein the processor executable instructions are further configured to cause the processor to cause a fluid inlet to add fluid at the outlet when more than one insect pupa passes the first secondary channel.

21. The insect pupae sorting system of claim 15, wherein the processor executable instructions are further configured to cause the processor to cause selective closure of the outlet to position the insect pupa for imaging.

22. An insect pupae sorting system, comprising:
a body;
a first channel formed in the body to transport a first flow of fluid comprising insect pupae, the first channel having a first dimension corresponding to a size of the insect pupae and comprising:
a pupae inlet at a first end of the first channel;
a first liquid inlet at a second end of the first channel, the first liquid inlet configured to introduce a first liquid flow into the first channel to change a flow direction in the first channel; and
a first liquid outlet at the second end of the first channel, the first liquid outlet configured to remove liquid from the first channel;
a second channel formed in the body that intersects the first channel between the pupae inlet and the first liquid inlet and provides a conduit between the first channel and a third channel, wherein the third channel is formed in the body and provides a conduit between a first pupae outlet and a second pupae outlet, the third channel intersected by the second channel between the first pupae outlet and the second pupae outlet;
a second liquid inlet adjacent the first pupae outlet; and
a third liquid inlet adjacent the second pupae outlet, the second liquid inlet and third liquid inlet configured to selectively deliver a second and third liquid flow into the third channel.

23. The insect pupae sorting system of claim 22, further comprising a fourth channel that intersects the first channel between the pupae inlet and the second channel, the fourth channel to deliver a fourth flow of liquid into the first channel to generate a fifth flow of liquid directable to the first liquid outlet, the first pupae outlet, or the second pupae outlet.

24. The insect pupae sorting system of claim 22, wherein the first channel comprises a tapered funnel section to guide insect pupae from the pupae inlet into the first channel.

25. The insect pupae sorting system of claim 22, wherein the first channel comprises:
a first portion having a first cross-sectional dimension; and
a second portion having a second cross-sectional dimension, wherein:
the second cross-sectional dimension is smaller than the first cross-sectional dimension; and
the first cross-sectional dimension enables the pupae to change direction within the first channel.

26. The insect pupae sorting system of claim 25, wherein the first portion has a first width and the first channel comprises a third portion having a second width, the second width smaller than the first width.

27. The insect pupae sorting system of claim 26, wherein the second portion is adjacent and in between each of the first portion and the third portion.

28. A method of imaging and sorting insect pupae, comprising:
providing a first flow of liquid comprising pupae into a first channel of an insect isolation device and through the first channel in a first direction, the first channel having a dimension corresponding to a size of a representative pupa of the pupae;
adjusting the first flow of liquid by introducing a second flow of liquid via a second channel to position an individual pupa in an imaging portion of the first channel;
capturing an image of the individual pupa using an optical sensor positioned between the second channel and a first and second pupae outlet;
determining a pupa type of the individual pupa based on the image; and
providing a third flow of liquid to sort the individual pupa into the first pupae outlet or the second pupae outlet based on the pupa type.

29. The method of claim 28, further comprising determining a number of pupae sorted into the first pupae outlet or the second pupae outlet.

30. The method of claim 29, wherein the optical sensor is positioned adjacent the first pupae outlet or the second pupae outlet, and wherein determining the number of pupae comprises receiving data from the optical sensor.

31. The method of claim 28, wherein adjusting the first flow of liquid comprises introducing the second flow of liquid in a second direction opposite the first direction.

32. The method of claim 28, wherein providing the second flow of liquid comprises opening the first pupae outlet or the second pupae outlet based on the pupa type.

33. The insect pupae sorting system of claim 1, wherein substantially all of the first flow of liquid, the second flow of liquid, and the third flow of liquid that enters the primary channel exits the primary channel at the outlet.

34. The insect pupae sorting system of claim 1, wherein the inlet of the primary channel is the only inlet of the primary channel and the outlet of the primary channel is the only outlet of the primary channel.

35. The insect pupae sorting system of claim 1, wherein the outlet is selectively operable between an open position and a closed position such that, when the outlet is in the closed position, a first insect pupae of the adjacent insect pupae is separated from other insect pupae of the adjacent insect pupae by remaining stagnant in the third flow of liquid while the other insect pupae are carried by the third flow towards the inlet of the primary channel.

* * * * *